United States Patent
Komata et al.

(10) Patent No.: US 6,548,712 B2
(45) Date of Patent: Apr. 15, 2003

(54) PROCESS FOR PRODUCING 1,1,1,5,5,5-HEXAFLUOROACETYLACETONE

(75) Inventors: Takeo Komata, Saitama (JP); Nariaki II, Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/808,105

(22) Filed: Mar. 15, 2001

(65) Prior Publication Data

US 2001/0034462 A1 Oct. 25, 2001

(30) Foreign Application Priority Data

Mar. 17, 2000 (JP) .......................... 2000-076838

(51) Int. Cl.⁷ .................. C07C 45/00; C07C 49/04; C07C 17/08; C07C 17/26; C07F 1/08
(52) U.S. Cl. .................. 568/394; 568/411; 568/418; 556/12; 556/112; 556/114; 570/167; 570/171
(58) Field of Search ................ 568/394, 411, 568/418; 556/12, 112, 114; 570/167, 171

(56) References Cited

U.S. PATENT DOCUMENTS 5,322,712 A * 6/1994 Norman et al.
5,663,391 A   9/1997 Machida et al. ............... 556/12
6,046,364 A   4/2000 Normal et al. ............... 568/306

OTHER PUBLICATIONS

Henne et al., "The Alkaline Condensation of Fluorinated Esters with Esters and Ketones", J. Amer. Chem. Soc., vol. 69 (1947) pp. 1819–1820.
Belford et al., "Influence of Fluorine Substitution on the Properties of Metal Chelate Compounds–I", Inorganic and Nuclear Chemistry, vol.2 (1956), pp. 11–31.
Gilman et al., "Organic Compounds of Uranium. I. 1, 3–Dicarbonyl Chelates", J. Amer. Chem. Soc., vol. 78 (1956), pp. 2790.
Copy of German office action with English translation.

* cited by examiner

Primary Examiner—Deborah D. Carr
Assistant Examiner—Sikarl A. Witherspoon
(74) Attorney, Agent, or Firm—Crowell & Moring LLP

(57) ABSTRACT

The invention relates to a process for producing 1,1,1,5,5,5-hexafluoroacetylacetone. This process includes (a) hydrolyzing a metal complex of 1,1,1,5,5,5-hexafluoroacetylacetone into a 1,1,1,5,5,5-hexafluoroacetylacetone hydrate; and (b) dehydrating the hydrate into the 1,1,1,5,5,5-hexafluoroacetylacetone with high purity from a material containing a metal complex of 1,1,1,5,5,5-hexafluoroacetylacetone.

19 Claims, No Drawings

PROCESS FOR PRODUCING 1,1,1,5,5,5-HEXAFLUOROACETYLACETONE

BACKGROUND OF THE INVENTION

The present invention relates to a process for producing or recovering 1,1,1,5,5,5-hexafluoroacetylacetone, which is useful as an intermediate for medicines and agricultural chemicals or an agent for a process producing electric parts and the like, and particularly to a process for producing or recovering this compound with high purity.

A large amount of a waste containing a metal complex of 1,1,1,5,5,5-hexafluoroacetylacetone is discharged and dumped, after the deposition of this metal complex by CVD in the production of electric parts. This dumping is not desirable from the viewpoints of the production cost and the environmental impact.

A. Henne et al., J. Amer. Chem. Soc., Vol. 69, pp. 1819–1820 (1947) discloses a process for producing anhydrous 1,1,1,5,5,5-hexafluoroacetylacetone by removing copper from a copper complex of 1,1,1,5,5,-hexafluoroacetylacetone with hydrogen sulfide in ether.

U.S. Pat. No. 6,046,364 discloses a process for recovering a 1,1,1,5,5,-hexafluoro-2,4-pentanedione ligand from a metal-ligand complex byproduct such as $Cu^{2+}(1,1,1,5,5,5$-hexafluoro-2,4-pentanedionate$^{-1})_2$, comprising: providing a copper-ligand complex byproduct of $Cu^{2+}(1,1,1,5,5,5$-hexafluoro-2,4-pentanedionate$^{-1})_2$ in a process stream; cooling and condensing the copper-ligand complex byproduct of $Cu^{2+}(1,1,1,5,5,5$-hexafluoro-2,4-pentanedionate$^{-1})_2$ to separate it from the process stream; contacting the copper-ligand complex byproduct of $Cu^{2+}(1,1,1,5,5,5$-hexafluoro-2,4-pentanedionate$^{-1})_2$ with a protonation agent, such as: sulfuric acid, hydrochloric acid, hydroiodic acid, hydrobromic acid, trifluoroacetic acid, trifluoromethanesulfonic acid, acid ion exchange resin, hydrogen sulfide, water vapor and mixtures thereof; and recovering 1,1,1,5,5,-hexafluoro-2,4-pentanedione. It is disclosed in this publication that the equation of using $H_2SO_4$ as the protonating agent in the Hhfac regeneration step is:

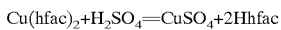

where (hfac) is 1,1,1,5,5,-hexafluoro-2,4-pentanedionate, and Hhfac is 1,1,1,5,5,-hexafluoro-2,4-pentanedione. It is further disclosed therein that hydrogen sulfide or water, typically as vapor, could be used as the protonation agents.

SUMMARY OF THE INVENTION

It is therefore an object of the present invention to provide a process for producing or recovering 1,1,1,5,5,5-hexafluoroacetylacetone from a metal complex of 1,1,1,5,5,5-hexafluoroacetylacetone.

It is another object of the present invention to provide a process for producing a 1,1,1,5,5,5-hexafluoroacetylacetone hydrate, which is an intermediate for 1,1,1,5,5,-hexafluoroacetylacetone, from a metal complex of 1,1,1,5,5,5-hexafluoroacetylacetone.

According to the present invention, there is provided a process for producing a 1,1,1,5,5,-hexafluoroacetylacetone hydrate. This process comprises hydrolyzing a metal complex of 1,1,1,5,5,-hexafluoroacetylacetone into said hydrate.

According to the present invention, there is provided a process for producing 1,1,1,5,5,5-hexafluoroacetylacetone. This process comprises (a) hydrolyzing a metal complex of 1,1,1,5,5,5-hexafluoroacetylacetone into a 1,1,1,5,5,5-hexafluoroacetylacetone hydrate; and (b) dehydrating said hydrate into said 1,1,1,5,5,5-hexafluoroacetylacetone

DESCRIPTION OF THE PREFERRED EMBODIMENTS

It is possible to recover 1,1,1,5,5,5-hexafluoroacetylacetone from a metal complex of 1,1,1,5,5,5-hexafluoroacetylacetone by a process of the invention. This process comprises (a) hydrolyzing this metal complex into a 1,1,1,5,5,5-hexafluoroacetylacetone hydrate (e.g., 1,1,1,5,5,5-hexafluoroacetylacetone dihydrate); and (b) dehydrating this hydrate into 1,1,1,5,5,5-hexafluoroacetylacetone. It is possible by this process to easily obtain 1,1,1,5,5,5-hexafluoroacetylacetone with high purity, which is usable for producing medicines and agricultural chemicals or processing electric parts.

The metal complex of 1,1,1,5,5,5-hexafluoroacetylacetone to be used in the invention is not particularly limited, and it may be one prepared by any process. For example, it may be one prepared by a process for producing 1,1,1,5,5,5-hexafluoroacetylacetone metal complexes. Furthermore, the metal complex may be one which has been recovered after its use in a film formation by CVD or in a purification for producing high purity metals.

The metal complex can be produced, for example, by reacting 1,1,1-trifluoroacetone with an ester of trifluoroacetic acid to obtain 1,1,1,5,5,5-hexafluoroacetylacetone and then by reacting this 1,1,1,5,5,5-hexafluoroacetylacetone with a metal compound (e.g., cuprous oxide, cuprous chloride and copper(II) sulfate) in a solvent. Metal of the metal complex is not particularly limited, and can be selected from copper, uranium, chromium, iron and the like. Of these, copper is the most preferable.

In order to achieve the object of the invention, it suffices that the metal complex contains at least one 1,1,1,5,5,5-hexafluoroacetylacetone as its ligand. In fact, it is preferable that each ligand of the metal complex is 1,1,1,5,5,5-hexafluoroacetylacetone.

Another ligand (other than 1,1,1,5,5,5-hexafluoroacetylacetone) of the metal complex (e.g., copper complex) can be selected from a hydrocarbon represented by the general formula (1), a cyclic hydrocarbon (optionally having a $C_5-C_{18}$ side chain containing at least two double bond) represented by the general formula (2), and an unsaturated compound represented by the general formula (3),

where $R^1$ and $R^2$ are hydrocarbon groups having a carbon atom number of 1–8 or silicon-containing organic groups having a carbon atom number of 1–8,

where $R^3$, $R^4$ and $R^5$ are hydrogen atoms or hydrocarbon groups having a carbon atom number of 1–6,

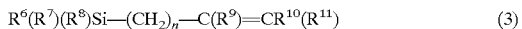

where $R^6$, $R^7$, $R^8$, $R^9$, $R^{10}$ and $R^{11}$ are hydrogen atoms, hydrocarbon groups having a carbon atom number of 1–6, or silicon-containing organic groups having a carbon atom number of 1–8; and n is 1 or 2. Concrete examples of the another ligand are trimethylvinylsilane (trimethylsilylethylene), triethylvinylsilane, 2-butyne, 1,5-cyclooctadiene, and cyclopentadiene.

Concrete examples of the metal complex are copper (II) bis(1,1,1,5,5,5-hexafluoroacetonato) and copper (II) (1,1,1, 5,5,5-hexafluoroacetylacetonato)-(trimethylsilylethylene). A more preferable example is copper (II) bis(1,1,1,5,5,5-hexafluoroacetonato).

In order to hydrolyze the metal complex in the process, it may contain impurities (e.g. a free 1,1,1,5,5,5-hexafluoroacetylacetone or a 1,1,1,5,5,5-hexafluoroacetylacetone hydrate).

The procedures of the hydrolysis can exemplarily be conducted as follows, and may be modified by a person skilled in the art. Such modification is also included in the invention. At first, a reaction vessel is charged with the metal complex (optionally containing impurities), followed by addition of water and then an acid to conduct the hydrolysis (acid hydrolysis). It suffices to add the water in an amount to make the reaction mixture in the form of an aqueous solution. Furthermore, it suffices to add the acid in a catalytic amount. After that, an extraction solvent is added to the reaction liquid, followed by separating the organic layer and then by removing the solvent from the organic layer, thereby obtaining 1,1,1,5,5,5-hexafluoroacetylacetone dihydrate in the form of solid. According to need, it is possible to increase the temperature of the reaction vessel during the reaction in order to accelerate the reaction.

The reaction vessel can be made of a material (i.e., glass or fluorine-containing resin) or lined with such material. The acid may be a mineral acid (e.g., sulfuric acid, hydrochloric acid and nitric acid). The reaction temperature of the hydrolysis may be about 0–110° C., preferably about 20–90° C. If it is lower than 0° C., the reaction rate may be too low. If it is higher than 110° C., the yield of 1,1,1,5,5,5-hexafluoroacetylacetone dihydrate may become too low.

After the hydrolysis, the resulting 1,1,1,5,5,5-hexafluoroacetylacetone hydrate can be extracted from a reaction mixture with an extraction solvent (e.g., ether solvents and halogen-containing solvents). This extraction solvent is, of course, in the form of liquid, when it is used. Its boiling point is not particularly limited, and is preferably about 100° C. or lower. Concrete examples of the ether solvent are diethyl ether, diisopropyl ether, diisobutyl ether, dibutyl ether, t-butyl methyl ether, tetrahydrofuran, anisole, and dioxane. Concrete examples of the halogen-containing solvent are methylene chloride, chloroform, carbon tetrachloride, 1,2-dichloroethane, 1,2-bis(trifluoromethyl)benzene, 1,3-bis(trifluoromethyl)benzene, 1,4-bis(trifluoromethyl)benzene, and 2,4-dichlorobenzotrifluoride. Of these, ether solvents are preferable, and t-butyl methyl ether is particularly preferable.

It is possible to dehydrate 1,1,1,5,5,5-hexafluoroacetylacetone dihydrate, which has been prepared in accordance with the invention, by a conventional method for dehydrating organic materials by contacting dehydrating agent, for example, concentrated sulfuric acid, phosphorus pentoxide, calcium sulfate and the like, thereby obtaining its anhydride. R. Belford, J. Inorganic and Nuclear Chemistry, 1956, Vol. 2, pp. 11–31 discloses such method in which a dispersion is prepared by shaking 1,1,1,5,5,5-hexafluoroacetylacetone dihydrate with approximately three times its volume of 98% sulfuric acid. After the dispersion has been allowed to stand overnight, dehydration of the product is repeated with a fresh batch of sulfuric acid. The resulting upper layer is siphoned off and distilled, thereby obtaining the anhydride (yield: 98%) as a distillate between 70.0–70.2° C. J. Amer. Chem. Soc., 78, 2790 (1956) discloses another method in which anhydrous calcium sulfate is mixed with 1,1,1,5,5,5-hexafluoroacetylacetone dihydrate. Then, the resulting mixture is heated. The distillate is again treated with anhydrous calcium sulfate and distilled, thereby obtaining the anhydride of a boiling point of 68° C. (736 mm.). There is known a still another method in which 1,1,1,5,5,5-hexafluoroacetylacetone dihydrate, together with phosphorus pentoxide, is heated in ether.

The following nonlimitative examples are illustrative of the present invention.

EXAMPLE 1

Preparation of 1,1,1,5,5,5-Hexafluoroacetylacetone Dihydrate

A 200-ml three-necked flask, equipped with a thermometer, a dropping funnel and a reflux condenser, was charged with 20.0 g (0.0417 moles) of copper(II) bis(1,1,1,5,5,5-hexafluoroacetylacetonato). Then, a mixture of 80 ml of water and 11.0 g (0.110 moles) of 98% sulfuric acid was added to the flask, while the reaction mixture was maintained at a temperature of not higher than 30° C. with stirring by a magnetic mixer. After the completion of this addition, the reaction was conducted for 6 hr at 50° C. After the reaction, the reaction mixture was cooled down to room temperature, followed by extraction with 50 ml of t-butyl methyl ether and then separation of the resulting organic layer. Then, 30 ml of t-butyl methyl ether were added to the water layer, followed by separation of the resulting organic layer. These organic layers were combined, followed by concentration using an evaporator, thereby obtaining 16.2 g of 1,1,1,5,5,5-hexafluoroacetylacetone dihydrate.

Production of 1,1,1,5,5,5-Hexafluoroacetylacetone

A 100-ml eggplant-type flask was charged with 16.2 g of the obtained 1,1,1,5,5,5-hexafluoroacetylacetone dihydrate and 33.0 g of 98% sulfuric acid. Then, the flask was stopped, and the mixture was stirred for 4 hr at room temperature with a magnetic mixer, followed by standing still for 1 hr to have two layers separated from each other. Then, 12.5 g of 1,1,1,5,5,5-hexafluoroacetylacetone were obtained from the organic layer. This product was found by a gas chromatography (detector: FED, column: DB-1, column size: 0.25 mm×60 m) to be 1,1,1,5,5,5-hexafluoroacetylacetone having a purity of 99.9% (areal % in gas chromatography).

EXAMPLE 2

Preparation of 1,1,1,5,5,5-Hexafluoroacetylacetone Dihydrate

The preparation of 1,1,1,5,5,5-hexafluoroacetylacetone dihydrate of Example 1 was repeated, thereby obtaining 16.5 g of 1,1,1,5,5,5-hexafluoroacetylacetone dihydrate.

Production of 1,1,1,5,5,5-Hexafluoroacetylacetone

A 100-ml glass reaction vessel, equipped with a thermometer, a stirrer and a reflux condenser filled with glass spheres, was charged with 16.5 g of the obtained 1,1,1,5,5,5-hexafluoroacetylacetone dihydrate and 33.0 g of 98% sulfuric acid, while nitrogen gas was allowed to flow through the reaction vessel. Then, the mixture was gradually heated to 80° C. with stirring by a magnetic mixer. During this heating, 12.3 g of a distillate of about 70° C. were collected. This distillate was found by the same gas chromatography as that of Example 1 to be 1,1,1,5,5,5-hexafluoroacetylacetone having a purity of 99.9%.

EXAMPLE 3

Preparation of 1,1,1,5,5,5-Hexafluoroacetylacetone Dihydrate

A 200-ml three-necked flask, equipped with a thermometer, a dropping funnel and a reflux condenser, was charged with 20.0 g of a copper(II) bis(1,1,1,5,5,5)-hexafluoroacetylacetonato (containing a large amount of impurities), that is, a condensate obtained by condensing in a liquid-nitrogen trap all of evaporates exhausted from a CVD film production line using copper(II) (1,1,1,5,5,5-hexafluoroacetylacetonato)(trimethylsilylethylene). Then, a mixture of 40 ml of water and 6.0 g of 98% sulfuric acid was added to the flask, while the reaction mixture was maintained at a temperature of not higher than 30° C. with stirring by a magnetic mixer. Then, the same procedures as those of Example 1 were conducted, thereby obtaining 12.8 g of 1,1,1,5,5,5-hexafluoroacetylacetone dihydrate.

Production of 1,1,1,5,5,5-Hexafluoroacetylacetone

A 20-ml eggplant-type flask was charged with 12.8 g of the obtained 1,1,1,5,5,5-hexafluoroacetylacetone dihydrate and 26.0 g of 98% sulfuric acid. Then, the flask was stopped, and the mixture was stirred for 4 hr at room temperature with a magnetic mixer, followed by standing still for 1 hr to have two layers separated from each other. Then, 9.8 g of 1,1,1,5,5,5-hexafluoroacetylacetone were obtained from the organic layer. This product was found by the same gas chromatography as that of Example 1 to be 1,1,1,5,5,5-hexafluoroacetylacetone having a purity of 99.9%.

EXAMPLE 4

Preparation of 1,1,1,5,5,5-Hexafluoroacetylacetone Dihydrate

The preparation of 1,1,1,5,5,5-hexafluoroacetylacetone dihydrate of Example 3 was repeated, thereby obtaining 12.5 g of 1,1,1,5,5,5-hexafluoroacetylacetone dihydrate.

Production of 1,1,1,5,5,5-Hexafluoroacetylacetone

A 100-ml glass reaction vessel, equipped with a thermometer, a stirrer and a reflux condenser filled with glass spheres, was charged with 12.5 g of the obtained 1,1,1,5,5,5-hexafluoroacetylacetone dihydrate and 25 g of 98% sulfuric acid, while nitrogen gas was allowed to flow through the reaction vessel. Then, the mixture was gradually heated to 80° C. with stirring by a magnetic mixer. During this heating, 9.5 g of a distillate of about 70° C. were collected. This distillate was found by the same gas chromatography as that of Example 1 to be 1,1,1,5,5,5-hexafluoroacetylacetone having a purity of 99.9%.

The entire disclosure of Japanese Patent Application No. 2000-076838 filed on Mar. 17, 2000, including specification, claims and summary, is incorporated herein by reference in its entirety.

What is claimed is:

1. A process for producing a 1,1,1,5,5,5-hexafluoroacetylacetone hydrate, said process comprising hydrolyzing a metal complex comprising 1,1,1,5,5,5-hexafluoroacetylacetone into said hydrate by adding water and an acid to said metal complex, said water being in an amount sufficient for said hydrolyzing.

2. A process for producing 1,1,1,5,5,5-hexafluoroacetylacetone hydrate by adding water and an acid to said metal complex, said water being in an amount sufficient for said hydrolyzing; and dehydrating said hydrate into 1,1,1,5,5,5-hexafluoroacetylacetone.

3. A process for recovering 1,1,1,5,5,5-hexafluoroacetylacetone from a material comprising a metal complex of 1,1,1,5,5,5-hexafluoroacetylacetone, said process comprising:

hydrolyzing said metal complex into a 1,1,1,5,5,5-hexafluoroacetylacetone hydrate by adding water and an acid to said metal complex, said water being in an amount sufficient for said hydrolyzing; and dehydrating said hydrate into said 1,1,1,5,5,5-hexafluoroacetylacetone.

4. A process according to claim 1, wherein said metal complex comprises copper.

5. A process according to claim 1, wherein said metal complex comprises at least one 1,1,1,5,5,5-hexafluoroacetylacetone as a ligand thereof.

6. A process according to claim 1, wherein each ligand of said metal complex is 1,1,1,5,5,5-hexafluoroacetylacetone.

7. A process according to claim 1, wherein said metal complex comprises copper(II) bis(1,1,1,5,5,5-hexafluoroacetylacetonato).

8. A process according to claim 1, wherein said metal complex comprises copper(II) (1,1,1,5,5,5-hexafluoroacetylacetonato)(trimethylsilylethylene).

9. A process according to claim 1, wherein said metal complex is prepared from 1,1,1,5,5,5-hexafluoroacetylacetone, said 1,1,1,5,5,5-hexafluoroacetylacetone being prepared by a process comprising reacting 1,1,1-trifluoroacetone with an ester of trifluoroacetic acid.

10. A process according to claim 9, wherein said metal complex is prepared by a process comprising reacting said 1,1,1,5,5,5-hexafluoroacetylacetone with a metal compound in a solvent.

11. A process according to claim 1, wherein said hydrolyzing is conducted at a temperature of about 0–110° C.

12. A process according to claim 1, wherein after said hydrolyzing, said 1,1,1,5,5,5-hexafluoroacetylacetone hydrate is extracted from a reaction mixture with a solvent.

13. A process according to claim 1, wherein said acid is a mineral acid.

14. A process according to claim 1, wherein said acid is sulfuric acid.

15. A process according to claim 12, wherein said solvent is an ether or a halogen-containing solvent.

16. A process according to claim 12, wherein said solvent has a boiling point of about 100° C. or lower.

17. A process according to claim 12, wherein said solvent is t-butyl methyl ether.

18. A process according to claim 1, wherein said acid is added in a catalytic amount.

19. A process for producing a 1,1,1,5,5,5-hexafluoroacetylacetone hydrate, said process comprising hydrolyzing a metal complex comprising 1,1,1,5,5,5-hexafluoroacetylacetone into said hydrate by adding water and an acid to said metal complex, said water being in an amount sufficient to make a reaction mixture into an aqueous solution, said reaction mixture comprising said metal complex, said water and said acid.

* * * * *